United States Patent [19]

Bos et al.

[11] Patent Number: 4,801,608

[45] Date of Patent: Jan. 31, 1989

[54] BISMUTH CONTAINING COMPOSITION AND METHOD FOR THE PREPARATION THEREOF

[75] Inventors: Petrus J. H. Bos, Schipluiden; Dirk J. C. Engel, Aerdenhout; Hayo de Jonge, Heemstede, all of Netherlands

[73] Assignee: Gist-Brocades N. V., Delft, Netherlands

[21] Appl. No.: 558,695

[22] Filed: Dec. 6, 1983

Related U.S. Application Data

[63] Continuation of Ser. No. 304,372, Sep. 22, 1981, abandoned.

[51] Int. Cl.[4] ...................... A61K 31/29; A61K 33/24
[52] U.S. Cl. .................................... 515/503; 424/131; 424/166; 514/925
[58] Field of Search ................ 424/131, 166; 514/503, 514/927

[56] References Cited

U.S. PATENT DOCUMENTS 3,920,792  11/1975  Beekman .............................. 424/157

FOREIGN PATENT DOCUMENTS 1414121  12/1972  United Kingdom ................ 424/157
1478742   7/1977  United Kingdom ................ 424/131

OTHER PUBLICATIONS

*Remington's Pharmaceutical Sciences,* 13th Ed. (1965) Mack Pub. Co., Easton, Pa. pp. 179 & 180.
*Current Medical Research and Opinion,* vol. 1, No. 10, 1973, pp. 629–634.
S. A. Medical Journal, vol. 42, Mar. 30, 1968, pp. 317–320.
*DE-NOL,* Bibliography, May 1982, R&D/Medical Department Gist-Brocades N.V.

*Primary Examiner*—Frederick E. Waddell
*Attorney, Agent, or Firm*—Emmanuel J. Lobato; Robert E. Burns

[57] ABSTRACT

A new solid bismuth containing composition which is colloidally soluble in water is obtained by spray drying an aqueous ammoniacal colloidal solution of bismuth citrate. The new composition is effective for the treatment of peptic ulcers.

25 Claims, No Drawings

BISMUTH CONTAINING COMPOSITION AND METHOD FOR THE PREPARATION THEREOF

This is a continuation, of application Ser. No. 304,372, filed Sept. 22, 1981, now abandoned.

BACKGROUND OF THE INVENTION

This invention relates to bismuth containing solid compositions and to a method for their preparation. More particularly, this invention concerns a solid bismuth composition which easily dissolves in water giving a colloidal solution, its preparation and use in pharmaceutical preparations for treatment of peptic ulcer.

A bismuth containing solid composition has been described in British Pat. No. 1,478,742. This known bismuth composition is obtained as a powder by spray drying a colloidal solution which is formed by solving in aqeuous ammonia bismuth citrate, which is a water insoluble compound, and a polyhydric alcohol, usually a sugar e.g. sucrose, sorbitol or mannitol.

The above-mentioned colloidal solution of bismuth citrate, ammonia and polyhydric alcohol has been used for some time and is still in use as the active principle of a therapeutically effective liquid anti-ulcer drug.

The effectiveness of this colloidal bismuth composition was surprising in view of the inactivity of the starting materials, including in particular, solid bismuth citrate in treating peptic ulcers.

Though this drug is very active in healing ulcers, the liquid form has certain disadvantages. The ammoniacal smell is unpleasant for patients taking the liquid; moreover, the liquid is awkward to manage, especially outdoors. Therefore, a solid form of this drug would be very desirable. However, the colloidal solution, being an hydrophobic, inorganic colloid, has been believed to be among the irreversible and irresoluble colloids. Since it is generally known that such systems, i.e., inorganic hydrophobic colloids always loose their colloidal properties during drying, for a long time no attempt was made to prepare a dry form of this drug.

Taking into account all previous experience with this type of hydrophobic colloidal systems, it was very surprising indeed to discover that the powder obtained in the above-described way and disclosed in British Pat. No. 1,478,742 can be redissolved in water without any expedient to provide again a colloidal solution. The colloidal properties of the resultant solution are easily shown by light scattering (Tyndall effect). It is generally known that when a beam of light passes a colloidal solution, a part of the light is scattered sideways.

The resultant solid product has been shown to be as active against ulcers as the original colloidal solution.

It was generally thought by people skilled in the art, that the colloidal solution of bismuth citrate, the spray-drying of which is described in the British patent mentioned above, must contain a compound which is able to stabilize the liquid, to improve its taste and to increase its viscosity considerably. A polyhydric alcohol, preferably a sugar such as sucrose matches all these requirements.

It has been believed that the above-mentioned phenomenon, i.e., ready reconstitution of a colloidal solution from the dried product of an inoganic hydrophobic colloid, previously unknown in the art of hydrophobic colloid chemistry, was the result of the large amount of solved sugar in the colloidal composition. The sugar was thought to prevent the clotting of the colloidal particles into larger insoluble aggregates, presumably due to a protecting layer with which each particle was thought to be coated during spray drying.

In order to stabilize hydrophobic colloids, it is known from prior art to apply compounds, often hydrophilic colloids, which like sugar have a strong interaction with the water structure, which compounds thus increase the viscosity of the colloidal system and lower the speed of flocculation. In fact, polyhydric alcohols, including sugars, are known to have a stabilizing effect on several colloidal systems and dispersions.

SUMMARY OF THE INVENTION

It was surprisingly found that a solution of bismuth citrate in aqueous ammonia can be dried satisfactorily in the absence of a polyhydric alcohol and surprisingly, the resultant powder obtained in this way, is still able to solve colloidally in water. Powder obtained by spray-drying an aqueous solution of bismuth citrate is, after combination with a polyhydric alcohol such as a sugar, against peptic ulcers as efficacious as a composition manufactured by spray-drying a solution in which the polyhydric alcohol is present.

In accordance with the present invention, a solid bismuth containing composition which is colloidally soluble in water is prepared by spray drying a colloidal solution of bismuth citrate in aqueous ammonia in the absence of polyhydric alcohol.

The solid product obtained by the described process is a feature of the invention. The solid product consists essentially of a complex of bismuth, citrate and hydroxyl ions and ammonia. The dry powder can be administered orally as such, but preferably it will be processed to a pharmaceutical composition or it may be dissolved in water to produce a palatable colloidal solution.

DETAILED DESCRIPTION OF THE INVENTION

A particular advantage of the process of the invention is that in the absence of polyhydric alcohol, it is possible to spray dry at higher temperatures. In sugar containing powders decomposition occurs at temperatures over 160° C., which leads to caking of the powder. The walls of the drying chamber become covered with a sticky layer where the sugar further decomposes. This means that the yield of pharmaceutically acceptable powder diminishes. Further, after spray-drying, the cleaning of the chamber entails a lot of work. These disadvantages disappear when the sugar is not added to the solution of bismuth citrate in liquid ammonia but if desired, only to the spray-dried powder.

The temperature of spray-drying in the present process can be raised to 210° C. and higher which means an increase in the drying capacity of at least 50%.

In carrying out the present process, the solution to be spraydried is fed to a conventional spray drier where it is sprayed, usually by means of a fast spinning rotor or by means of one or more nozzles and the resultant spray is contacted with an air stream which has been heated to a temperature of about 160°–250° C., more preferably 200°–220° C. The temperature of the air stream at the outlet of the drier is about 80°–120° C., more preferably 90°–100° C.

To remove periodically or continuously possible deposits of spray-dried product on the walls of the drying chamber, the unit is provided with known means as are an installation which automatically knocks against the outerside of the chamber wall, or with an air broom within the chamber.

The colloidal solution is prepared by dissolving bismuth citrate in aqueous ammonia. Desirably up to about 44% (w/v) of bismuth citrate is dissolved in water, using enough ammonia to keep the bismuth salt in colloidal solution.

Preferably about 0.3 to 2.0 g of ammonia per g. of bismuth citrate and more preferably about 0.6 to 1.2 g of ammonia per g. of bismuth citrate is added and most preferably about 0.9-1.1 g of ammonia per g of bismuth citrate is added.

The colloidal solution to be spray-dried contains bismuth citrate in an amount of up to about 44% (w/v), more preferably in an amount of about 10 to 30% (w/v) and most preferably in an amount of about 20 to 25% (w/v) and ammonia in an amount of about 8–33% (w/v) and preferably in an amount of about 20 to 25% (w/v).

Addition of about 15–45% potassium hydroxide and about 0–40% citric acid to the solution to be spraydried gives extra protection against the formation of a precipitate. Preferably, about 30% of potassium hydroxide and about 17% of anhydrous citric acid are added. The percentages are by weight and based on the amount of bismuth citrate.

However, the amounts of added potassium hydroxide and citric acid cannot be varied fully independently of each other. Attention should be given to the pH of the initial colloidal solution which should be kept in the range of about 8–11.3, otherwise, a precipitate may be formed.

The concentration of the solution is such that the solid content is about 20 to 50% (w/v), preferably about 30–40% (w/v) and most preferably about 33% (w/v).

The spray dried product contains a complex of bismuth, citrate and hydroxyl ions and ammonia and may also contain residual water in an amount up to about 5% by weight. It has been found that compositions of the invention must contain at least 3% ammonia. If less ammonia is present the composition is not colloidally soluble in water and/or does not form a stable colloidal solution. Given the applied spray drying conditions no more than 5% ammonia will be retained in the powder.

Preferably the solid composition of the invention contains about 32 to 52% by weight and more preferably 39–42% by weight of bismuth calculated as $Bi_2O_3$.

It has been found, surprisingly, that the spray dried product of the invention readily dissolves in water to reform a colloidal solution. No special expedient or additives are necessary to effect the dissolution of the solid bismuth composition of the invention; ordinary water at a pH of about 7 is all that is required to reconstitute a colloidal solution.

The invention also includes pharmaceutical compositions in dosage form for oral administration, such as sachets, capsules, a syrup, effervescent tablets or other oral tablets, e.g. chewing tablets, containing the therapeutically active dry bismuth preparation as the active ingredient. Polyhydric alcohols may be added to the dried or to a reconstituted aqueous colloidal solution, in an amount preferably less than 250% of the amount of bismuth citrate present in the starting solution. The polyhydric alcohol is selected from the group consisting of sucrose, maltose, fructose, glucose, mannitol, sorbitol and glycerol. Sucrose is preferred.

The sucrose can be substituted by mannitol, which is less hygroscopic and less cariogenic, or by another polyhydric alcohol combined, if desired, with an artificial sweetener such as sodium saccharine or sodium cyclamate.

Also, some other expedients such as coloring and flavoring agents, and preservatives, may be preference by added after spraydrying.

The compositions may further contain pharmaceutically acceptable carriers.

The tablets may be formulated in the usual manner with one or more pharmaceutically acceptable diluents or excipients, for example, lactose or starch and include materials of a lubricating nature, for example, calcium stearate or magnesium stearate. Capsules made of absorbable materials, such as gelatin, may contain the active substance alone or in admixture with a solid or liquid diluent.

The compositions according to the invention in solid form or in the form of a reconstituted aqueous colloidal solution are therapeutically effective in the treatment of peptic ulcer, including gastric, duodenal and postoperaive ulcer and peptic ulcer associated with hiatus hernia.

Suitable daily dosages for adult humans contain bismuth corresponding to 450–1000 mg. of $Bi_2O_3$. The dosage for children will depend on their weight and age and may be calculated by methods commonly used in medical practice. The daily dose for children under 10 years will correspond to 150–400 mg. of $Bi_2O_3$.

The pharmaceutical compositions in dosage forms therefore preferably have a bismuth content equivalent to 35–250 mg. of $Bi_2O_3$.

The invention is further illustrated by the following examples:

EXAMPLE 1

180.360 kg. bismuth citrate
180.360 kg. ammonia (25%)
31.170 kg. citric acid monohydrate
52.120 kg. potassium hydroxide (85% pure)

are solved in water. The solution is diluted until the concentration of solids is 33% (w/v) and is then fed to a spray-drying unit which has been preheated by hot air. The unit has a evaporative capacity of about 450 kg. of water per hour. The bismuth citrate solution is atomized by means of a fast spinning rotor. At the same time the unit is supplied with an air stream heated at a temperature of 200°–220° C. This air dries the spray and carries the powder from the drying unit to at least one cyclone where the powder is separated from the air. At the outlet of the drying unit the temperature of the air stream has fallen to 90°–100° C. After leaving the drying chamber, the stream is mixed with cooler air, so that the dried powder collected in the last cyclone is at or about ambient temperature.

The unit is provided with an installation which automatically knocks against the outside of the chamber to remove possible deposits on the walls.

The products obtained from a series of runs carried out in the foregoing manner have been analyzed for bismuth, ammonia and water with the following results:

$Bi_2O_3$: 39–42%
$NH_3$: 3–4%
$H_2O$: 5% or less
pH: 6–8 percentages except $H_2O$ related to dry matter only.

EXAMPLE 2

Using known pharmaceutical techniques, tablets are prepared, containing 450 mg. of the spray-dried product prepared according Example 1, and further
 900 mg. of mannitol
 10 mg. of Aerosil 200 (purified silicum dioxide)
 100 mg. of corn starch
 10 mg. of magnesium stearate
 1 mg. of sodium saccharine The invention also includes within its scope the preparation of an aqueous solution from the dry powder. For instance, a solution suitable for oral administration may be obtained by dissolving 200 g. of the powder prepared according to Example 1 in water to a volume of 1 liter. Other physiologically acceptable substances may be added, for instance, to produce a desired pH or to improve the taste of the solution.

What is claimed is:

1. In a process for the preparation of a solid bismuth containing composition which is colloidally soluble in water by spray drying a colloidal solution of bismuth citrate in aqueous ammonia, wherein the colloidal solution contains a polyhydric alcohol and optionally potassium hydroxide or a combination of potassium hydroxide and citric acid in amounts such that the pH of the colloidal solution is in the range of about 8 to 11.3, the improvement comprising spray drying a colloidal solution of bismuth citrate in aqueous ammonia in the absence of a polyhydric alcohol in the solution to be spray dried.

2. The process according to claim 1 which is carried out at a temperature of about 200°–220° C.

3. The process according to claim 1 or 2 in which the colloidal solution contains 0.3 to 2 gram ammonia per gram of bismuth citrate.

4. The process according to claim 1 or 2 in which the colloidal solution contains 0.6 to 1.2 gram ammonia per gram of bismuth citrate.

5. The process according to claim 1 or 2 in which the colloidal solution contains 0.9–1.1 gram ammonia per gram of bismuth citrate.

6. The process according to claims 1 or 2 in which the colloidal solution contains up to 44% (w/v) of bismuth citrate.

7. The process according to claim 1 or 2 in which the colloidal solution contains 10 to 30% (w/v) of bismuthcitrate.

8. The process according to claim 1 or 2 in which the colloidal solution contains 20–25% (w/v) of bismuthcitrate.

9. The process according to claim 1 or 2 in which the colloidal solution contains 8–33% (w/v) of ammonia.

10. The process according to claim 1 or 2 in which the colloidal solution contains 20–25% (w/v) of ammonia.

11. Solid bismuth containing composition prepared according to claim 1.

12. A process for preparing a pharmaceutical composition which comprises combining the solid bismuth containing composition obtained according to claim 1 in an amount effective for the treatment of ulcer with a pharmaceutically acceptable carrier.

13. The process for the preparation of a pharmaceutical composition according to claim 12 in which a polyhydric alcohol in an amount not surpassing 250% of the amount of bismuth citrate is added to said composition.

14. A pharmaceutical composition prepared by the process of claim 12.

15. A solid bismuth composition useful for treating peptic ulcers which is colloidally soluble in water at a pH of about 7 and which consists of a complex of bismuth, citrate and hydroxyl ions and ammonia and optionally potassium hydroxide or a combination of potassium hydroxide and citrate ions, wherein said ammonia is present in an amount of about 3 to 5% by weight.

16. The solid bismuth composition according to claim 15 in which bismuth, calculated as $Bi_2O_3$ is present in an amount of about 39–42% by weight.

17. The solid bismuth composition according to claim 15 or 16 in which said composition forms a substantially stable colloidal solution in water containing no additives at a pH of about 7.

18. A pharmaceutical composition containing a composition defined in claim 15 in an amount effective for the treatment of ulcers in combination with a pharmaceutically acceptable carrier.

19. The process defined in claim 1 in which said colloidal solution of bismuth citrate in aqueous ammonia also contains about 15 to 45% by weight of potassium hydroxide and 0 to 40% by weight of citric acid based on the weight of said bismuth citrate to protect said colloidal solution against the formation of precipitate, the amount of said potassium hydroxide and citric acid being such that the pH of said colloidal solution is in the range of about 8 to 11.3.

20. The process according to claim 1 in which said colloidal solution contains 10 to 30% (w/v) of bismuth citrate and 0.6 to 1.2 grams of ammonia per gram of bismuth citrate and in which the spray drying is carried out at a temperature of 200° to 220° C.

21. The process according to claim 19 in which said colloidal solution contains 10 to 30% (w/v) of bismuth citrate and 0.6 to 1.2 grams of ammonia per gram of bismuth citrate and in which spray drying is carried out at a temperature of 200° to 220° C.

22. The process according to claim 1 in which the colloidal solution contains 20 to 25% (w/v) of bismuth citrate and 0.9 to 1.1 grams of ammonia per gram of bismuth citrate, and in which said spray drying is carried out at a temperature of about 200° to 220° C.

23. The process according to claim 19 in which the colloidal solution contains 20 to 25% (w/v) of bismuth citrate and 0.9 to 1.1 grams of ammonia per gram of bismuth citrate and in which said spray drying is carried out at a temperature of about 200° to 220° C.

24. The process according to claim 1 in which said colloidal solution of bismuth citrate in aqueous ammonia consists of 10 to 30% (w/v) of bismuth citrate and 8 to 33% (w/v) of ammonia.

25. The process according to claim 1 in which said colloidal solution of bismuth citrate in aqueous ammonia consists of 10 to 30% (w/v) of bismuth citrate, 0.3 to 2 g. of ammonia per g. of bismuth citrate, 15 to 45% by weight of potassium hydroxide based on the weight of bismuth citrate and 0 to 40% by weight of citric acid based on the weight of bismuth citrate, the amount of said potassium hydroxide and said citric acid being such that the pH of said colloidal solution is in the range of about 8 to 11.3.

* * * * *